United States Patent [19]
Tomita et al.

[11] Patent Number: 4,980,043
[45] Date of Patent: * Dec. 25, 1990

[54] REFERENCE ELECTRODE

[75] Inventors: Katsuhiko Tomita; Haruo Kotani, both of Kyoto, Japan

[73] Assignee: Horiba, Ltd., Kyoto, Japan

[*] Notice: The portion of the term of this patent subsequent to Jan. 10, 2006 has been disclaimed.

[21] Appl. No.: 124,903

[22] Filed: Nov. 24, 1987

[30] Foreign Application Priority Data

Dec. 11, 1986 [JP] Japan ................................. 61-191498
Jul. 4, 1987 [JP] Japan ................................. 62-168375

[51] Int. Cl.$^5$ ............................................. G01N 27/30
[52] U.S. Cl. .................................... 204/414; 204/433; 204/435
[58] Field of Search ........................ 204/414, 435, 433

[56] References Cited

U.S. PATENT DOCUMENTS 3,705,089 12/1972 Grubb ................................. 204/414

FOREIGN PATENT DOCUMENTS

2541462 8/1984 France .

Primary Examiner—G. L. Kaplan
Attorney, Agent, or Firm—Price, Gess & Ubell

[57] ABSTRACT

In a sheet type reference electrode having a gelatinized internal solution, a liquid junction surface of the gelatinized internal solution is coated with a hydrophilic porous thin film. Alternatively, a liquid junction member contacts the gelatinized internal solution and is coated with a hydrophilic porous thin film. In either event, the thin film controls the diffusion of ions from the gelatinized internal solution. A liquid junction portion is also provided by impregnating a chemically stabilized, hydrophilic, high molecular porous material with a gelatinized composition which remains wet.

15 Claims, 10 Drawing Sheets

REFERENCE ELECTRODE

BACKGROUND OF THE INVENTION

1. Field of the Invention

The present invention generally relates to a reference electrode used as a standard electrode for a measuring electrode in the measurement of an ion-concentration of a solution. More specifically, the present invention relates to an improved sheet type or tube type reference electrode and an improved liquid junction.

2. Description of Related Work of the Inventors

Recently, the present inventors have developed an epoch-making sheet type electrode that exhibits various kinds of advantages. It can be remarkably small-sized, easily mass-produced, and remarkably low in the cost of production. It is also remarkably superior in operation and maintenance in place of electrodes for use in the measurement of ion-concentration (measuring electrodes, reference electrodes and composite electrodes thereof) of conventional type (test tube type) and various kinds of progressive improvements for them. They have been already disclosed in detail in many applications for patent and utility model by the present applicants, such as Japanese Utility Model application Ser. No. Sho 60-97385 and Japanese patent application Ser. No. Sho 61-285371.

Figure 11:
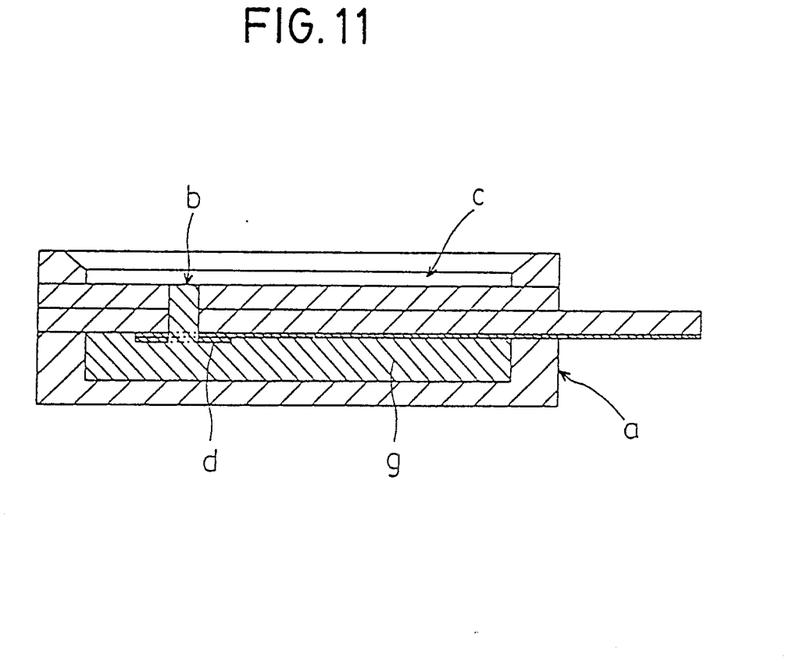
FIG. 11 is a longitudinal, sectional view showing a sheet type reference electrode (portion) having a construction showing a related work in this field by the inventors.

As shown in FIG. 11, such a sheet type reference electrode (or a reference electrode portion in a sheet type composite electrode for use in the measurement of ion-concentration) has a gelatinized internal solution "g" enclosed in a support frame member "a" so that a liquid junction surface "b" of the gelatinized internal solution "g" may be exposed over a sample solution-dropping portion "c." An internal electrode "d" which is coated with an electrode material, such as AgCl, is formed so as to be brought into contact with the gelatinized internal solution "g." In addition, the gelatinized internal solution "g" is formed by adding a gelatinizer, such as agar-agar, and a water-evaporation inhibitor, such as glycerine, to a fundamental internal solution (for example, a 3.3 M-aqueous solution of KCl supersaturated with AgCl with a phosphoric acid buffer solution added). The details of the solution have been already disclosed in Japanese patent application Ser. No. Sho 61-63564 filed by the present applicants.

However, with the above described sheet type electrode, the liquid junction surface "b" of the gelatinized internal solution "g" is adapted to be directly brought into contact with the sample solution. Therefore, it is almost impossible to control the quantity of ions ($K^+$, $Cl^-$) which leak (diffuse) from the gelatinized internal solution "g" when used. Accordingly, a problem occurs in that the concentration of the gelatinized internal solution "g" is apt to be lowered in a comparatively short time. Since it is impossible to exchange the gelatinized internal solution "g", the useful life of the electrode as a whole is limited, and a problem of accuracy in measurement exists.

SUMMARY OF THE INVENTION

The present invention was achieved in view of the above described disadvantages. Objects of the present invention are to remarkably improve the useful lifetime of an electrode and the accuracy of measurement by remarkably satisfactorily controlling the quantity of ions diffused from the gelatinized internal solution, in spite of using means superior for mass-production.

Figure 1A:
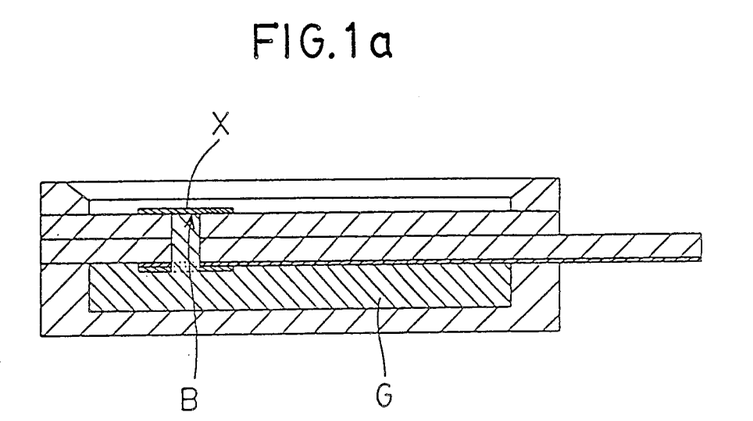
FIG. 1(A), (B) is a longitudinal, sectional view showing a fundamental construction of a liquid junction structure in a reference electrode according to the present invention.
Figure 1B:
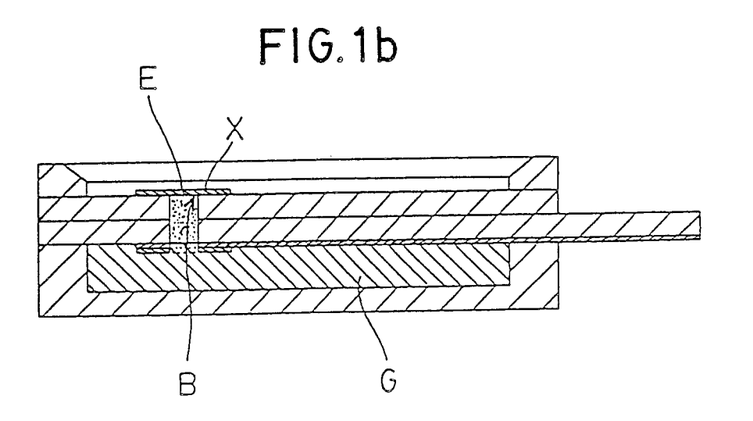

In order to achieve the above described objects, a liquid junction structure in a sheet type reference electrode having a fundamental construction as described above is characterized by a liquid junction surface B of a gelatinized internal solution G, or a liquid junction member E connected to the gelatinized internal solution G for a sample solution, which is coated with a hydrophilic porous thin film X, as shown in FIG. 1(A) and (B).

Such a characteristic construction exhibits the following effects:

With the above described liquid junction structure in a sheet type reference electrode according to the present invention, the liquid junction surface B of the gelatinized internal solution G, or the liquid junction member E connected to the gelatinized internal solution G for the sample solution, is coated with the hydrophilic porous thin film X so as not to be brought into direct contact with the sample solution. The entire thin film X takes part in the control of the diffusion of ions from the gelatinized internal solution G, whereby the quantity of ions diffused can be always maintained constant for a long time without being influenced by the concentration condition of the gelatinized internal solution G. In addition, once the water-evaporation inhibitor, such as glycerine which is included in the gelatinized internal solution G, is introduced into the hydrophilic porous thin film X, a surface of the hydrophilic porous thin film X remains wet to form an ideal liquid junction portion. Thus, the useful lifetime of the electrode and the accuracy of measurement can be remarkably improved. Moreover, this hydrophilic porous thin film X can be easily mass-produced so that it can be very inexpensively produced.

BRIEF DESCRIPTION OF THE DRAWINGS

In addition, the preferred embodiments, to which a sheet type reference electrode according to the present invention is applied, are shown in FIGS. 2 to 10, in which.

DESCRIPTION OF THE PREFERRED EMBODIMENTS

The preferred embodiments of the present invention are below described with reference to the drawings.

Figure 2:
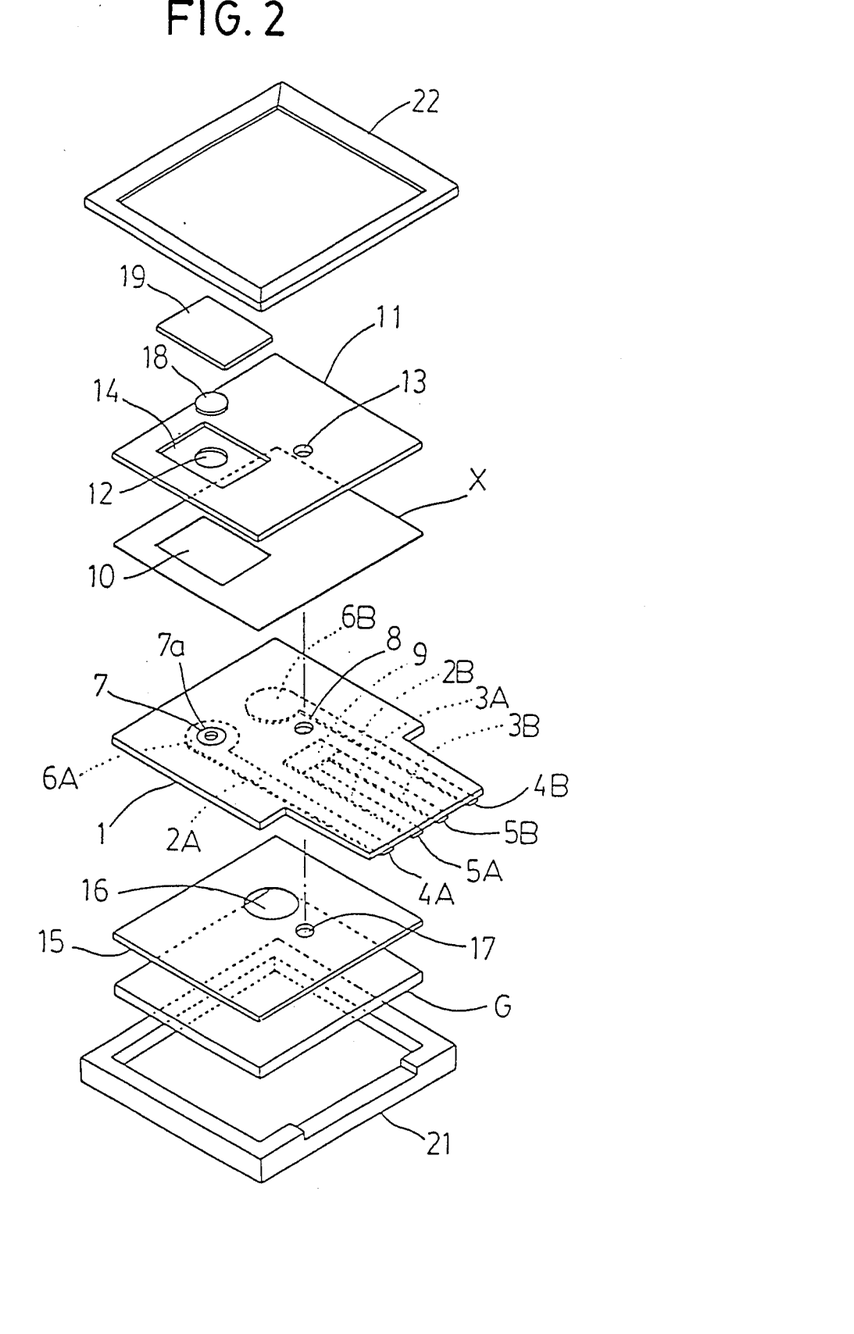
FIG. 2 is an exploded, perspective view showing a pH-measuring sheet type composite electrode according to a first preferred embodiment.
Figure 3:
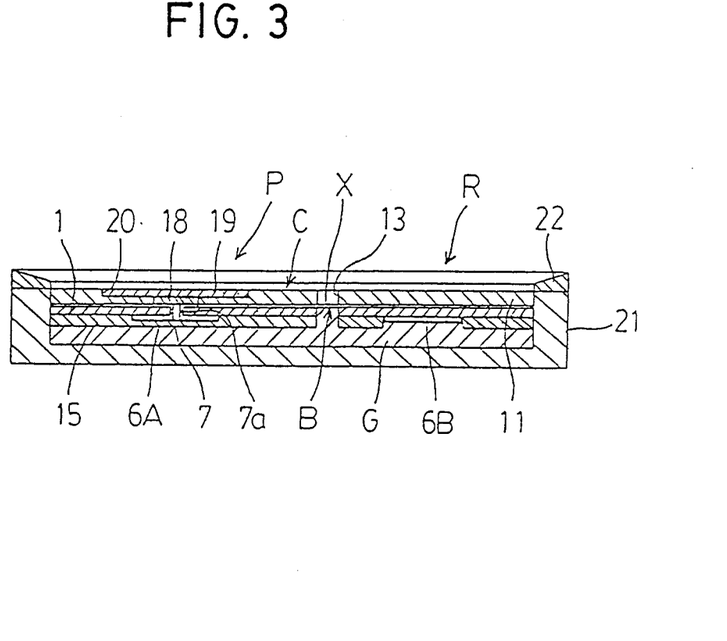
FIG. 3 is a developed longitudinal, sectional view showing principal parts of the first preferred embodiment.

An exploded, perspective view in FIG. 2 and a developed longitudinal, sectional view showing principal parts in FIG. 3 show a first preferred embodiment of a sheet type composite electrode for use in the measurement of pH and which applies the present invention.

Referring to FIGS. 2 and 3, reference numeral 1 designates a substrate formed of a material (for example, organic high molecular weight materials, such as polyethylene, polypropylene, polyethylene terephthalate, acrylic resin and polyfluoroethylene; and inorganic materials, such as silica glass and PYREX glass) having a sufficiently high electrical insulating property even though it is immersed in a solution including electrolytes (in the present preferred embodiment, a polyethylene terephthalate plate). The substrate 1 is provided with two pairs of electrodes—an inside pair of electrodes 3A, 3B and an outside pair of electrodes 2A, 2B—stuck to a lower surface side of the substrate 1. The electrodes are so fixed by depositing metals selected from a group consisting of electrically conductive Ag, Cu, Au, Pt and the like and alloys thereof or a paste comprising the metals or semiconductors, such as $IrO_2$ and $SnO_2$, by physical plating methods, such as the vacuum vapor deposition method and the CVD method; or chemical plating methods, such as the electrolytic method and the non-electrolytic method; or printing methods, such as the silk screen method, the anastatic method and the flat plate method.

In the present preferred embodiment, the lower surface of the substrate 1 is subjected to a grafting process and an anchoring treatment by a silane coupling agent and the like. Then, an Ag paste is printed on it by a silk screen method. In addition, a base end portion positioned at one end edge portion of the substrate 1 in each of the electrodes 2A, 2B, 3A, 3B is formed as lead portions 4A, 4B, 5A, 5B, respectively.

Nearly circular pointed end portions positions at nearly a central portion of the substrate 1 in the outside pair of electrodes 2A, 2B are formed as internal electrode portions 6A, 6B. The internal electrode portions are coated with an electrode material, such as AgCl, by means of physical plating methods, chemical plating methods, printing methods or the like in the same manner as above described. One internal electrode portion 6A (a side of pH-measuring electrode portion P) is provided with a through hole 7, of which the inside surface is subjected to an electrifying treatment, and thereby serves as an electrode-through hole formed at a nearly central portion thereof. Reference number 7a designates an electrified portion of the through hole 7. A through hole 8 is also provided in the substrate 1 in the vicinity of the other internal electrode portion 6B (a side of reference electrode portion R). A temperature-compensating electrode portion 9, such as a thermistor, is provided and extends between the pointed end portions of the inside pair of electrodes 3A, 3B of said substrate 1.

Reference mark X designates a hydrophilic porous thin film provided on the upper surface of the substrate 1. The film X is provided with a hole 10 formed at a place corresponding to the through hole 7 formed in the substrate 1 and its circumferential electrified portion 7a. In the present preferred embodiment, a hydrophilic polypropylene film (trade name: DURAGURD No. 3400; thickness: 25 microns; the largest hole diameter: $0.02 \times 0.2$ microns) is used as this hydrophilic porous thin film X. The hydrophilic porous thin film X is laminated on the upper surface of the substrate 1, excepting the through hole 8. This is accomplished by a hot melting method using adhesives (for example, polyolefine series adhesives, silicone resin series adhesives and the like) which are capable of securing a sufficiently high electrical insulating property (for example, 10 M$\Omega$ or more).

The hydrophilic porous thin film X includes various kinds of material, such as PVC, polycarbonate, polyester, ABS, polytetrafluoroethylene, polyurethane, cellulose, cellulose acetate, polyacrylonitril, polymethylmethacrylate, polyethylene vinyl acetate and polysulfone, in addition to the above described polyolefine series materials, such as polypropylene and polyethylene. Also, hydrophobic materials can be sufficiently used by subjecting them to an $H_2O$ plasma treatment and a silane coupling treatment to give a hydrophilic property.

In addition, the hydrophilic porous thin film X is not limited to a one-layer structure. For example, a multilayer structure having a plurality of hydrophilic porous thin films may be used. Each layer may have the same pore-diameter or different pore-diameters, with the layers piled up. Thus, the quantity of ions diffused can still be easily and accurately controlled.

Reference numeral 11 designates a first support layer formed of a material having a sufficiently high electrical insulating property in the same manner as the substrate 1 (in the present preferred embodiment, polyethylene terephthalate). The support layer 11 is provided with through holes 12, 13 formed at places respectively corresponding to the through holes 7, 8 formed in the substrate 1. An indented portion 14 is formed on a circumference of an upper side of the through hole 12, and is provided on an upper surface of the hydrophilic porous thin film X by, for example, the screen printing method or the hot melting method using adhesives (for example, polyolefine series adhesives, silicone resin series adhesives and the like). The support layer 11 is capable of securing a sufficiently high electrical insulating property (for example, 10 M$\Omega$ or more) or the like. Also, an upper surface of the first support layer 11 is subjected to a grafting process and an anchoring treatment by a silane coupling agent and the like.

Additionally, the hydrophilic porous thin film X may be previously laminated on a lower surface of the first support layer 11.

Reference numeral 15 designates a second support layer formed of a material having a sufficiently high electrical insulating property in the same manner as the substrate 1 and the first support layer 11 (in the present preferred embodiment, polyethylene terephthalate). The second support layer 15 is provided with through holes 16, 17 which are formed at places corresponding to the internal electrode portion 6B of a side of the reference electrode R and the through hole 8 formed in the substrate 1, respectively. The second support layer 15 is provided on the lower surface of the substrate 1 in the same manner as the first support layer 11.

Reference numeral 18 designates a gelatinized internal solution to be charged in the through hole 12 of a side of the pH-measuring electrode portion P in the first support layer 11. The gelatinized internal solution 18 is formed by adding a gelatinizer (for example, agar-agar, gelatine, glue, alginic acid, various kinds of water-absorbing polymer and the like) and a water-evaporation inhibitor (for example, glycerine, ethylene glycol and the like) to a fundamental internal solution obtained by adding a phosphoric acid buffer solution to a 3.3. M-aqueous solution of KCl supersaturated with AgCl. The resulting mixture is then molded in a disc-like shape. The gelatinized internal solution 18 is filled in the through hole 12 by heating to turn it into a paste. The resulting paste is printed by the screen printing method and the like so that its upper surface may slightly project over the upper surface of the first support layer 11. The gelatinized internal solution 18 is sealed up tightly in the through hole 12 and connected to the internal electrode portion 6A through the electrified portion 7a of the through hole 7. This seal is accomplished by fixing a flat, plate-like, pH-response membrane 19, which is formed to have an appointed size, to an upper surface of the gelatinized internal solution 18 at a lower surface of the membrane 19.

Reference numeral 20 designates adhesives having a sufficiently high electrical insulating property (for example, organic high molecular adhesives, such as silicone series adhesives, epoxy series adhesives and urethane series adhesives) for fixedly mounting the gelatinized internal solution 18 in the indented portion 14 of the first support layer along a circumference thereof.

Reference mark G designates a relatively large-sized, rectangular shaped, gelatinized internal solution for use in the reference electrode portion and which is inserted in a bottom case 21. The solution G has the same composition as the gelatinized internal solution 18 on the side of the pH-measuring electrode portion P. The gelatinized internal solution G is brought into contact with not only the internal electrode portion 6B through the through hole 16 of the second support layer 16, but also the lower surface of the hydrophilic porous thin film X through the through hole 17 (so that each portion may be risen). In addition, a surface where the gelatinized internal solution G is brought into contact with the hydrophilic porous thin film X is herein called a liquid junction surface B.

Reference numeral 22 designates a frame member fixedly mounted on an upper surface of a circumference of the first support layer 11 and is provided with a sample solution-dropping portion C formed on an internal side thereof.

With the pH-measuring sheet type composite electrode having the above described construction, the liquid junction surface B of the gelatinized internal solution G of the side of the reference electrode portion R is coated with the hydrophilic porous, thick film X. Thereby, the surface B is not brought into direct contact with the sample solution introduced into the sample solution-dropping portion C. Accordingly, the diffusion of ions from the gelatinized internal solution G can be controlled by the thin film X to maintain the quantity of ions diffused at a constant value for a long time. As a result, a useful lifetime of the electrode and the accuracy of measurement can be remarkably improved.

Figure 4:
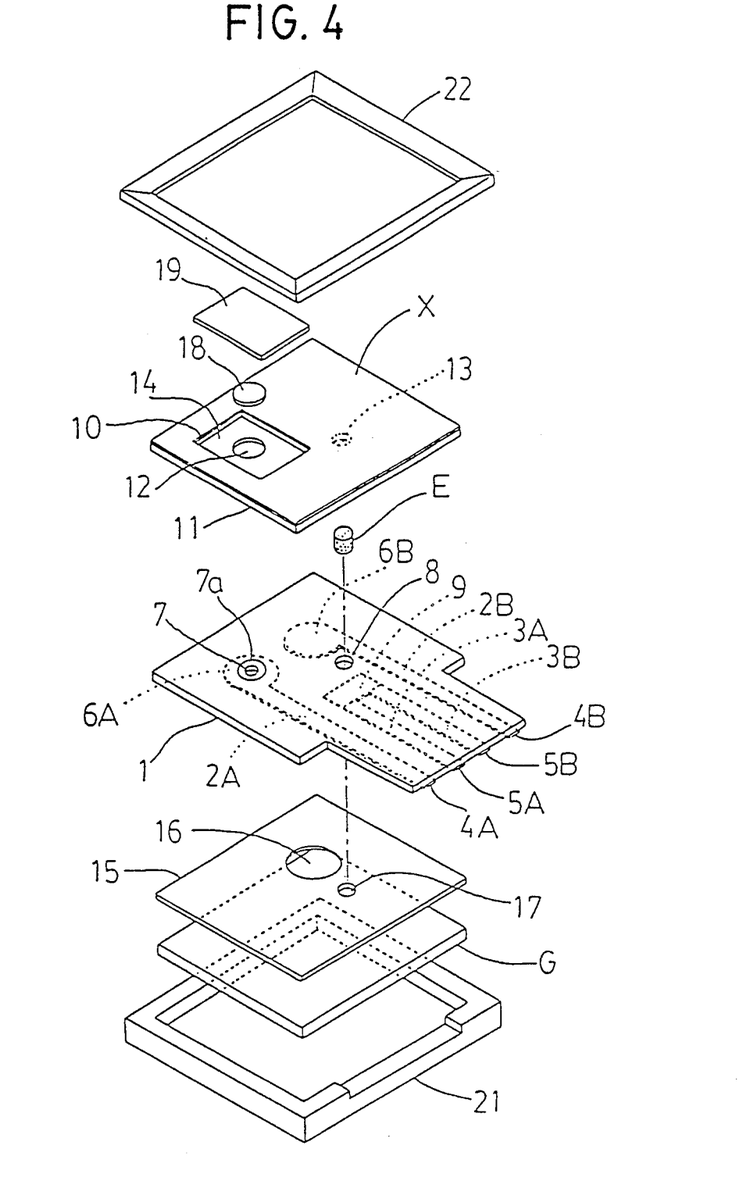
FIG. 4 is an exploded, perspective view showing a pH-measuring, sheet type, composite electrode according to a second preferred embodiment.
Figure 5:
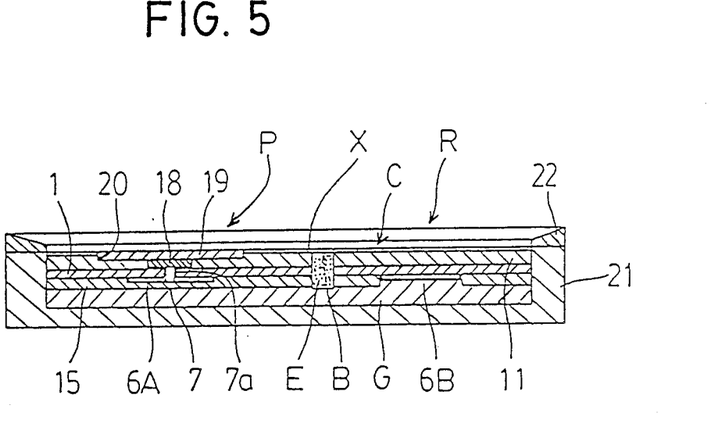
FIG. 5 is a developed, longitudinal, sectional view showing principal parts of the pH-measuring, sheet type, composite electrode according to the second preferred embodiment.

An exploded perspective view in FIG. 4 and a developed longitudinal section view showing principal parts in FIG. 5 depict a pH-measuring sheet type composite electrode according to a second preferred embodiment. In this case, a hydrophilic porous thin film X is laminated on an upper surface of a first support layer 11. A liquid junction member E, which is formed of a columnar gel-impregnated hydrophilic high molecular porous material, is provided so as to extend over a through hole 13 of the first support layer 11, a through hole 8 of a substrate 1, and a through hole 17 of a second support layer 15 in an inserted manner. A liquid junction surface B, which is an upper surface of the liquid junction member E, is brought into contact with a lower surface of the hydrophilic porous thin film X. A lower surface of the liquid junction member E is brought into contact with a gelatinized internal solution G of a side of a reference electrode R.

This liquid junction member E is formed by impregnating a sintered molded product of olefinic high polymer powders having nearly the same mechanical strength as, for example, polyolefine. It also has a hydrophilicity given by the transformation treatment (for example, SUNFINE AQ—trade name—manufactured by Asahi Kasei Kogyo Co., Ltd.) as a hydrophilic high molecular porous material formed by sintering and molding chemically stabilized hydrophilic high molecular powders with a gelatinized composition, which does not dry out when left unattended in air, such as a water-containing jelly mainly comprising sodium salt of acrylic polymer (for example, U-jelly (trade name) manufactured by Showa Denko Co., Ltd.).

In this second preferred embodiment, since the liquid junction member E that prevents a dry-out phenomenon is put between the hydrophilic porous thin film X and the gelatinized internal solution G, a useful life of the gelatinized internal solution G can be maintained for a still longer time.

Other constructions, operations and the like are similar to those in the first preferred embodiment; members having the same function are marked with the same reference numerals and their description is omitted.

In the first and second preferred embodiments, a liquid junction structure in a sheet type reference electrode exhibits superior efforts. A quantity of ions diffused from a gelatinized internal solution can be very satisfactorily controlled, whereby a remarkable improvement in useful lifetime of electrode and accuracy of measurement is achieved. This is achieved in spite of using a remarkably simple and superior mass-productivity means, namely, by using a liquid junction surface of the gelatinized internal solution, or a liquid junction member connected to the gelatinized internal solution for a sample solution, which is coated with a hydrophilic porous thin film.

Other preferred embodiments of the present invention are below described with reference to FIGS. 6 to 10.

Figure 6:
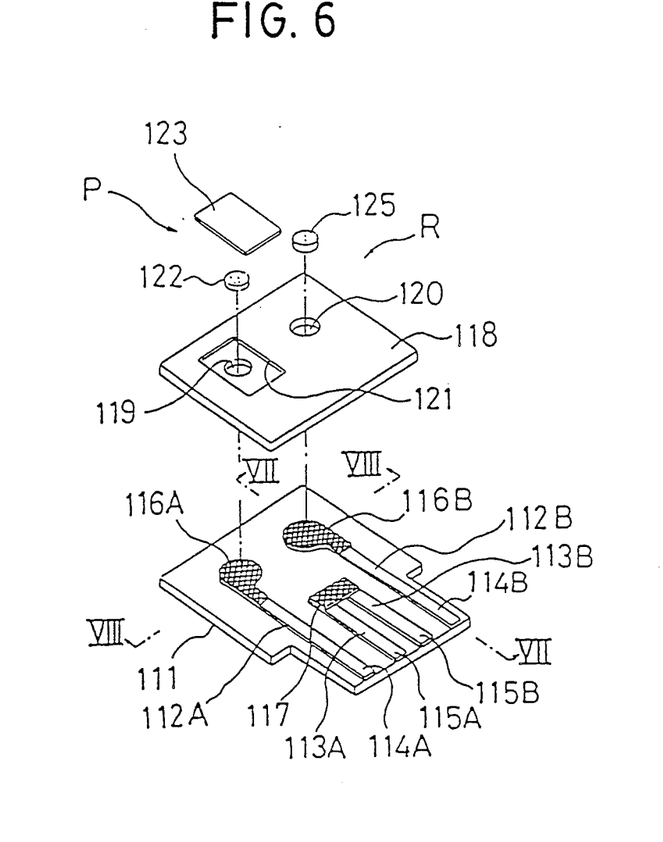
FIG. 6 is an exploded, perspective view showing an ion-measuring, sheet type, composite electrode according to a third preferred embodiment.
Figure 7:
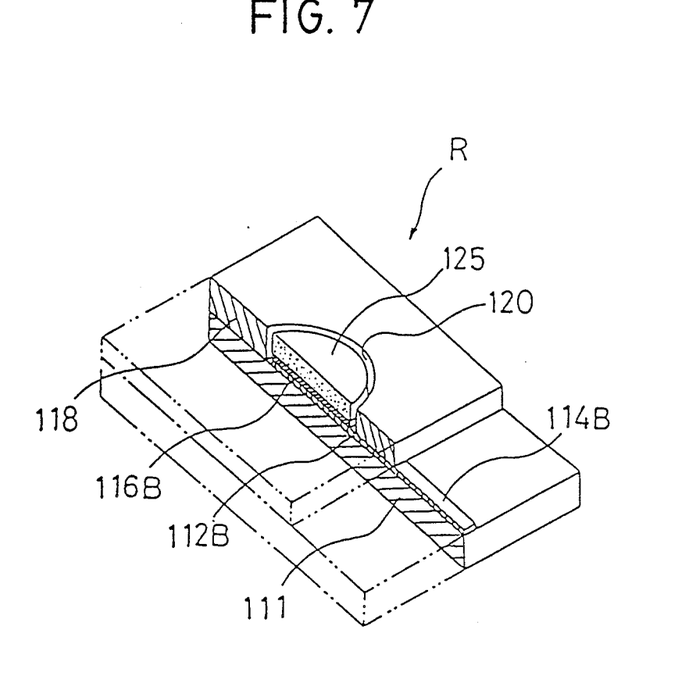
FIG. 7 is a sectional view of FIG. 6 taken along the line VII—VII thereof.
Figure 8:
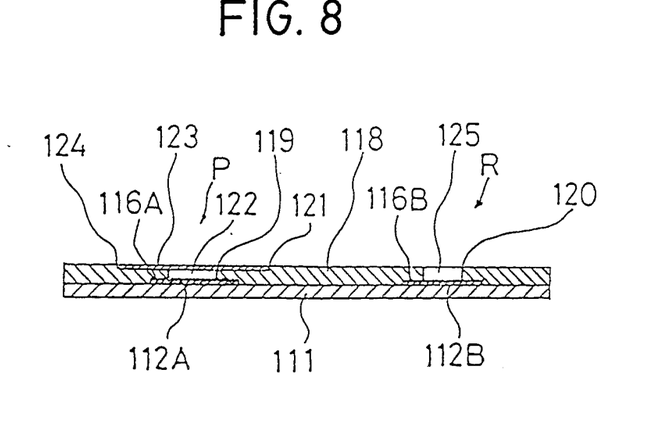
FIG. 8 is a sectional view of FIG. 6 taken along the line VIII—VIII thereof.

FIGS. 6 to 8 show a sheet type composite electrode for use in the measurement of pH. Reference mark 111 designates a substrate formed of materials (in the present preferred embodiment, a polyethylene terephthalate plate) having a sufficiently high electrical insulating property even when immersed in a solution including electrolytes, such as organic high molecular materials (for example, polyethylene, polypropylene, polyethylene terephthalate, acryl, polyfluoroethylene and the like) and inorganic materials (for example, silica glass, PYREX glass and the like). The substrate 111 is provided with two pairs of electrodes—an inside pair of electrodes 113A, 113B and an outside pair of electrodes 112A, 112B.

The electrodes are formed by sticking a metal selected from a group consisting of electrically conductive Ag, Cu, Au, Pt and the like, alloys thereof and the like, or a paste including said metal, or a semiconductor, such as $I_rO_2$ and $SnO_2$, to an upper surface of the substrate 111 by a physical plating method, such as vacuum deposition method and CVD method; or a chemical plating method, such as electrolytic method and non-electrolytic method; or a printing method, such as silk screen method, anastatic printing and flat plate printing. In the present preferred embodiment, the upper surface of the substrate 111 is subjected to a graft processing and an anchoring process by a silane coupling agent and the like and then, an Ag paste is printed on the upper surface of the substrate 111 by the silk screen printing method.

In addition, each base end portion positioned at one end edge portion of the substrate 111 in each electrode 112A, 112B, 113A, 113B is formed as lead portions 114A, 114B, 115A, 115B, respectively. The other nearly circular pointed end portions positioned at a nearly central portion of the substrate 111 in the outside pair of electrodes 112A, 112B are formed as internal electrode portions 116A, 116B, respectively. The portions 116A, 116B are coated with an electrode material, such as AgCl, by physical plating methods or chemical plating methods or printing methods in the same manner as above described. A temperature-compensating electrode portion 117 is provided and extends over and between other pointed end portions in the inside pair of electrodes 113A, 113B and positioned at a nearly central portion of the substrate 111. For example, a thermistor and the like are used as the temperature-compensating electrode portion 117.

Reference numeral 118 designates a support layer provided on an upper surface of the substrate 111 and which is formed of a material having a sufficiently high electrical insulating property in the same manner as the substrate 111 (in the present preferred embodiment, a polyethylene terephthalate layer). The support layer 118 is provided with an indented portion 121 formed on an upper surface side of the layer 118 so as to have an appointed size and the indented portion 121 includes a through hole 119. The support layer 118 also describes a through hole 120, whereby through holes 119, 120 are formed at places corresponding to the internal electrode portions 116A, 116B, respectively, formed in the substrate 111.

The support layer 118 is formed by, for example, a screen printing method or a heat fusion means using adhesives (for example, polyolefine series adhesives, silicone resin series adhesives and the like) which are capable of securing the sufficiently high electrical insulating property (for example, 10 MΩ or more). Also, an upper surface of the support layer 118 is subjected to a grafting process and an anchoring process by a silane coupling agent and the like.

Reference numeral 122 designates a gelatinized internal solution charged in the through hole 119 of the support layer 118 and formed in, for example, a disc-like shape. The solution 122 is made by adding a gelatinizer (for example, agar-agar, gelatine, glue, alginic acid, various kinds of acrylic water-absorbing polymer and the like) and a gel-evaporation inhibitor (for example, glycerine, ethylene glycol and the like) to a fundamental internal solution obtained by, for example, adding a phosphoric acid buffer solution to a 3.3 M-aqueous solution of KCl supersaturated with AgCl.

The gelatinized internal solution 122 is filled in the through hole 119 by heating it to turn it into a paste and then printing the resulting paste by the screen printing method so that an upper surface thereof may slightly project over an upper surface of the support layer 118 under a free condition. The solution 122 is sealed up tightly in the through hole 119 by providing a flat, plate-like, selective ion-response membrane 123, which is formed so as to have an appointed size. A lower surface of the flat plate-like selective ion-response membrane 123 contacts the upper surface of the support layer 118, and is thereby brought into contact with the internal electrode portion 116A to construct a pH-measuring electrode P.

Reference numeral 124 designates adhesives, for example, high molecular adhesives such as a silane coupling agent, having a sufficiently high electrical insulating property for sticking the selective ion-response membrane 123 to the support layer 118 along a circumference thereof.

Reference numeral 125 designates a gel-impregnated, hydrophilic, high molecular porous material charged so as to be inserted into the through hole 120 formed in the support layer 118. The gel-impregnated, hydrophilic, high molecular porous material 125 functions as a combination liquid junction and internal solution portion of the reference electrode R.

The gel-impregnated, hydrophilic, high molecular porous material 125 is formed by impregnating a hydrophilic high molecular porous material, which is obtained by sintering and molding chemically stabilized hydrophilic high molecular particles, for example, sintered and molded olefinic high polymeric powders having a mechanical strength nearly equal to that of polyolefines, to which the hydrophilicity is given by a modification treatment, (for example, SUNFINE AQ (trade name) manufactured by Asahi Kasei Kogyo Co., Ltd.) with a gelatinized composition, which does not deposit KCl and lose the wetness from a surface of the porous material; that is to say, it does not dry out, even when left unattended in air.

The above described gelatinized composition is obtained by dissolving a high moisture-preserving water-contained jelly mainly comprising acrylic polymers (for example, U-jelly (trade name) manufactured by Showa Denko Co., Ltd.) in the internal solution obtained by, for example, adding a phosphoric acid buffer solution to a 3.3 M-aqueous solution of KCl supersaturated with AgCl and then adding a gelatinizer selected from a group consisting of agar-agar, gelatine, glue, alginic acid and the like to the resulting solution.

The U-jelly, as the high humidity-holding water-contained jelly, was originally developed by Showa Denko Co., Ltd. as a base agent for a cosmetic cream. It is a transparent water-contained jelly mainly comprising sodium salt of acrylic polymer having a remarkably high compatibility with other aqueous solutions and remarkably superior to the conventional moisture-evaporation inhibitor, such as glycerine and propylene gylcol, in moisture-holding function and vapor pressure equilibrium-holding function. This is due to the formation of clusrate by hydrogen bonds between polymeric molecules. Accordingly, this jelly can maintain a sufficient lubricity for a long time without drying out even though it is exposed to air for a long time, and the absorption of water in air and dewing are hardly produced. As a result, it has a characteristic wherein its surface can be always maintained under a moderately wet condition.

Figure 9:
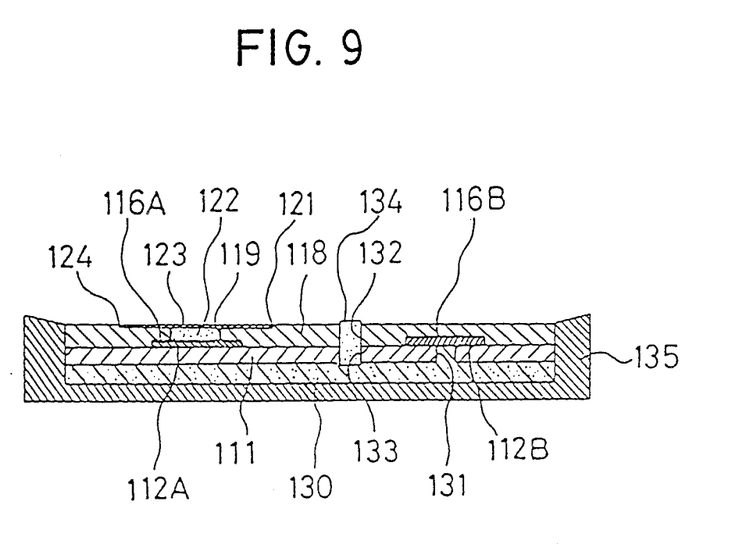
FIG. 9 is a partially developed, sectional view showing a fourth preferred embodiment of the present invention.

Although the combination liquid junction and internal solution portion of a side of the reference electrode R is formed of a side of the gel-impregnated hydrophilic high molecular porous material 125, it may be formed in such a manner as shown in FIG. 9.

Referring to FIG. 9, reference numeral 130 designates a gelatinized internal solution having the same composition as the gelatinized internal solution 122 described in the above described preferred embodiment and is provided on a lower surface of the substrate 111. The substrate 111 is provided with a through hole 131 which is formed at a place corresponding to the internal electrode portion 116B (of a side of the reference electrode R). Thereby, the gelatinized internal solution 130 is brought into contact with the internal electrode portion 116B through the through hole 131.

In addition, the substrate 111 and the support layer 118 are provided with through holes 133, 132, respectively, at corresponding positions so as to communicate with each other. A gel-impregnated, hydrophilic, high molecular porous material 134, which is formed in the same manner as the above described gel-impregnated hydrophilic high molecular porous materials 125, is inserted into the through holes 132, 133 so that a lower end thereof may be brought into contact with the gelatinized internal solution 130. In addition, reference numeral 135 designates a bottom case.

With the above described construction, the gel-impregnated hydrophilic high molecular porous material 134, constituting the liquid junction portion, is connected to the lead portion 112B through the gelatinized internal solution 130.

Figure 10:
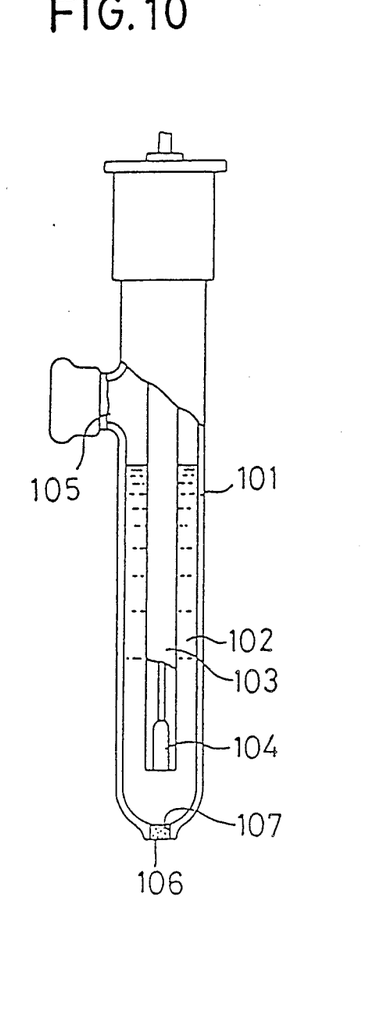
FIG. 10 is a partial, sectional view showing a cylindrical reference electrode according to a fifth preferred embodiment of the present invention.

FIG. 10 shows a fifth preferred embodiment of the invention.

Referring to FIG. 10, reference numeral 101 designates a support tube formed of glass or plastics and houses an internal solution 102, such as an aqueous solution of KC1. An internal electrode 104 is formed in an end portion of a glass tube 103. Reference numeral 105 designates a supply port for the internal solution 102. Reference numeral 106 designates a gel-impregnated, hydrophilic, high molecular porous material that acts as a liquid junction portion as is formed in an end portion of the support tube 101. The material 106 is formed in the same manner as the above described gel-impregnated, hydrophilic, high molecular porous materials 125, 135 and is inserted into a hole 107 formed in the end portion of the support tube 101.

In a reference electrode constructed in the above described manner, the gel-impregnated, hydrophilic, high molecular porous material is obtained by impregnating the chemically stabilized hydrophilic high molecular porous material with the gelatinized composition, which does not dry out even when left unattended in air, and is used as the liquid junction portion 106. Therefore, not only is the liquid junction portion 106 stabilized in shape but also the internal solution 102 does not flow out, whereby it becomes unnecessary to replenish the internal solution 102. Moreover, since the gelatinized composition, with which the hydrophilic high molecular porous material is impregnated, does not dry out, meshes of the liquid junction portion can be prevented from being clogged. Also, measurements can be always carried out under the wet condition; and as a result, a stabilized measurement can be achieved.

Additionally, since the gel-impregnated, hydrophilic, high molecular porous material constructed in the above described manner does not swell and reduce its strength, and it is superior in size stability, it can be easily incorporated in the support member 101 formed of glass and plastics.

In addition, the gel-impregnated, hydrophilic, high molecular porous material can be formed on the support member 101 as the liquid junction portion 106 by the use of suitable adhesives according to materials of the support member 101.

According to the reference electrode of the above third, fourth and fifth embodiments, since a gel-impregnated, hydrophilic, high molecular porous material, which is formed by impregnating a chemically stabilized hydrophilic high molecular porous material with a gelatinized composition which does not dry out even when left unattended in air, is used as a liquid junction portion, the reference electrode exhibits effects in that it can be preserved and stabilized measurements can be achieved.

What is claimed is:

1. A reference electrode, comprising:
   a planar, gelatinized internal solution formed by adding a gelatinizing agent and a water-evaporation inhibitor to an internal solution; and
   one of a liquid junction surface of said gelatinized internal solution and a liquid junction member connected to said gelatinized internal solution, both of which are for receiving a sample solution, and both of which are coated with a hydrophilic porous film, said film having a multi-layer construction such that layers are stacked upon one another.

2. In a sheet-type composite electrode for use in the measurement of ions, an improved liquid junction portion, comprising:
   a gel-impregnated, hydrophilic, high molecular weight porous material which is formed by impregnating a chemically stabilized, hydrophilic, high molecular weight porous material with a gelatinized composition which remains wet even when left unattended in air, said liquid junction portion extending through a first throughhole in a first support insulating layer, a second throughhole in a second support insulating layer, and a third throughhole in a planar, insulating substrate having an electrode, said substrate being intermediate said support layers, said liquid junction portion contacting a planar gelatinized internal solution positioned at a side of said second support layer which is opposite to that side adjacent said substrate and a hydrophilic film that receives a sample and is positioned at a side of said first support layer which is opposite that side adjacent said substrate.

3. The improvement of claim 2 wherein the gelatinized composition includes a water-containing jelly.

4. The improvement of claim 2 wherein the film is made of polypropylene.

5. The improvement of claim 4 wherein the film is a multi-layered structure.

6. A sheet type composite electrode for use in the measurement of ions, comprising:

a substrate having a high electrical insulating property with an electrode thereon and with first and second substrate holes therein;

a first support layer disposed over an upper surface of the substrate and having a high electrical insulating property with first and second holes therein;

a second support layer disposed over a lower surface of the substrate and having a high electrical insulating property with first and second throughholes therein;

a gelatinized internal solution in contact with a lower surface of the second support layer such that the second support layer is intermediate the substrate and the internal solution;

one of the first hydrophilic porous film on a bottom surface of the first support layer such that said film is intermediate the first support layer and the substrate, and a second hydrophilic porous film on an upper surface of the first support layer, said first and second films having a film hole therein which is aligned with said first hole and first substrate hole; and one of a liquid junction surface of the gelatinized internal solution that contacts the first hydrophilic porous thin film and a liquid junction member that contacts the gelatinized internal solution and contacts the second hydrophilic porous thin film, said liquid junction member extending through said second hole, second substrate hole, and second throughhole.

7. The reference electrode of claim 6 further comprising an electrode fixed intermediate the substrate and the second support layer.

8. The reference electrode of claim 6 wherein the liquid junction member is positioned in the through holes.

9. A sheet-type composite electrode for use in the measurement of ions, comprising:

a planar substrate having an upper surface and a bottom surface opposite thereto;

an electrode on said bottom surface;

a planar, gelatinized internal solution having a gelatinizing agent and a water evaporation inhibitor, said internal solution covering said electrode from said bottom surface; and one of a liquid junction surface of said internal solution being above said upper surface of said substrate and a liquid junction member connected to said internal solution and extending through said substrate, said junction surface being a top surface of a portion of said internal solution that extends generally perpendicular from a planar portion thereof, said junction member having a longitudinal length that extends generally perpendicular to said planar portion, both of said liquid junction surface and liquid junction member being coated with a hydrophilic porous film.

10. The reference electrode of claim 9 wherein said hydrophilic porous film is thin and has a multi-layer structure in which a plurality of films having one of a same pore diameter and different pore diameters are piled up.

11. The reference electrode of claim 9 wherein the gelatinizing agent is agar-agar.

12. The reference electrode of claim 9 wherein the water-evaporation inhibitor is glycerine.

13. The reference electrode according to claim 9 further including a first support layer disposed across said upper surface and intermediate said porous film and substrate.

14. The reference electrode according to claim 9 further including a first support layer which is positioned such that said porous film is intermediate said first support layer and substrate.

15. A sheet-type composite electrode for use in the measurement of ions, said electrode having a flat, insulating substrate; two pairs of flat electrodes on the substrate; and an insulating support layer disposed adjacent two opposed sides of said substrate, comprising:

a planar, gelatinized internal solution formed by adding a gelatinizing agent and a water-evaporation inhibitor to an internal solution is positioned beneath said insulating support layer; and one of a planar liquid junction surface of said gelatinized internal solution and a liquid junction member with a planar surface and connected to and above said gelatinized internal solution, both of said junction surface and junction member and for receiving a sample solution, and both of which are coated with a hydrophilic porous film, said film having a hole defined therein which aligns with an internal portion of an electrode assembly and can receive a response membrane.

* * * * *